(12) United States Patent
Lee

(10) Patent No.: US 11,039,871 B2
(45) Date of Patent: Jun. 22, 2021

(54) SUBPERIOSTEAL SYRINGE DEVICE FOR ADMITTING BONE GRAFT MATERIAL INTO A SUBPERIOSTEAL LOCUS

(71) Applicant: Ernesto A. Lee, Bryn Mawr, PA (US)

(72) Inventor: Ernesto A. Lee, Bryn Mawr, PA (US)

( * ) Notice: Subject to any disclaimer, the term of this patent is extended or adjusted under 35 U.S.C. 154(b) by 18 days.

(21) Appl. No.: 15/631,835

(22) Filed: Jun. 23, 2017

(65) Prior Publication Data

US 2018/0368901 A1    Dec. 27, 2018

(51) Int. Cl.
| | | |
|---|---|---|
| *A61B 17/88* | (2006.01) | |
| *A61L 27/58* | (2006.01) | |
| *A61L 27/36* | (2006.01) | |
| *A61F 2/28* | (2006.01) | |
| *A61L 27/54* | (2006.01) | |

(52) U.S. Cl.
CPC ...... *A61B 17/8825* (2013.01); *A61B 17/8816* (2013.01); *A61L 27/3608* (2013.01); *A61L 27/58* (2013.01); *A61F 2002/2835* (2013.01); *A61L 27/54* (2013.01); *A61L 2400/06* (2013.01); *A61L 2430/02* (2013.01)

(58) Field of Classification Search
CPC ............ A61B 17/8825; A61B 17/8816; A61B 17/8802; A61B 17/064; A61B 2017/8838
See application file for complete search history.

(56) References Cited

U.S. PATENT DOCUMENTS

| | | |
|---|---|---|
| 1,608,275 A | 2/1922 | Grier et al. |
| 4,340,060 A | 7/1982 | Berke et al. |
| 4,820,306 A | 4/1989 | Gorman et al. |
| 5,085,638 A | 2/1992 | Farbstein et al. |
| 5,295,827 A | 3/1994 | Fundingsland et al. |
| 5,372,503 A | 12/1994 | Elia |
| 5,695,338 A | 12/1997 | Robert |

(Continued)

FOREIGN PATENT DOCUMENTS

| | | |
|---|---|---|
| WO | 2014033898 A1 | 3/2014 |
| WO | WO2014033898 A1 | 3/2014 |

(Continued)

OTHER PUBLICATIONS

Michael S. Block, DMD et al.; Horizontal Ridge Augmentation Using Human Mineralized Particulate Bone: Preliminary Results; American Association of Oral Maxillofacial Surgeons, 2004; J Oral Maxillofac Surg 62:67-72, 2004, Suppl 2.

(Continued)

*Primary Examiner* — Andrew Yang
(74) *Attorney, Agent, or Firm* — Bonini IP Law, LLC; Frank J. Bonini, Jr.

(57) ABSTRACT

A subperiosteal syringe assembly for storing, containing and delivering bone graft material to a location within the tissue of a jaw for use in a medical procedure. The syringe assembly has a lumen body that is maneuverable within the subperiosteal tissue to deposit bone graft material at the desired surgical site. Embodiments include a lumen body that has a flat shape, such as an elliptical shape. A plunger is provided to deliver the syringe contents. The syringe may be loaded with bone graft material, and some embodiments may be supplied pre-loaded with bone graft material. An end cap seals the open end of the lumen, and may function as a septum that may be punctured with a needle to introduce a liquid substance, such as a growth factor, into the lumen where the bone material is stored. The syringe may be designed to incorporate surgical navigation and laparoscopic systems.

43 Claims, 11 Drawing Sheets

(56) References Cited

U.S. PATENT DOCUMENTS

| | | | |
|---|---|---|---|
| 6,086,592 | A | 7/2000 | Rosenberg et al. |
| 6,102,932 | A | 8/2000 | Kurz |
| 6,273,720 | B1 | 8/2001 | Spalten |
| 6,309,219 | B1 | 10/2001 | Robert |
| 6,554,803 | B1 | 4/2003 | Ashman |
| 6,575,749 | B1 | 6/2003 | Greenwald |
| 6,926,699 | B2 | 8/2005 | Stone |
| 6,994,548 | B2 | 2/2006 | Perret, Jr. |
| 7,357,789 | B2 | 4/2008 | Bills |
| 8,968,323 | B2 | 3/2015 | McKay |
| 9,060,877 | B2 * | 6/2015 | Kleiner ............... A61F 2/4455 |
| 9,242,779 | B1 | 1/2016 | Schildcrout |
| 9,427,335 | B2 * | 8/2016 | Ponticiello ............... A61F 2/28 |
| 2002/0151769 | A1 | 10/2002 | Kim |
| 2003/0032925 | A1 | 2/2003 | Stone |
| 2004/0068234 | A1 | 4/2004 | Martin et al. |
| 2004/0111066 | A1 | 6/2004 | Prais et al. |
| 2007/0031788 | A1 | 2/2007 | Chao |
| 2011/0183287 | A1 | 7/2011 | Lee |
| 2012/0330368 | A1 | 12/2012 | Dunn |
| 2015/0054195 | A1 | 2/2015 | Greyf |
| 2015/0105785 | A1 * | 4/2015 | Kapec ................. A61M 37/00 606/94 |
| 2017/0311999 | A1 * | 11/2017 | Vogt ................. A61B 17/8833 |

FOREIGN PATENT DOCUMENTS

| | | |
|---|---|---|
| WO | 2015/037838 A1 | 3/2015 |
| WO | WO2015037838 A1 | 3/2015 |

OTHER PUBLICATIONS

Oscar Hasson, DDS et al.; "Augmentation of deficient lateral alveolar ridge using the subperiosteal tunneling dissection approach"; Kaplan Medical Center; Oral Surg Oral Med Oral Pathol Oral Radiol Endod 2007, vol. 103, No. 3, e14-e19.

Efraim Kfir, DDS, et al.; "Minimally Invasive Guided Bone Regeneration"; Journal of Oral Implantology, vol. XXXIII, No. Four, 205-210, 2007.

Marc l. Nevins, DMD, MMSc et al.; "Minimally Invasive Alveolar Ridge Augmentation Procedure (Tunneling Technique) Using rhPDGF-BB in Combination with Three Matrices A case Series", The International journal of Periodontics & Restoraive Dentistry, vol. 29, No. 4, 370-385, 2009, Quintessence Publishing Co. Inc.

Feng Xuan, MD, et al.; "Vertical Ridge Augmentation Using Xenogenous Bone Blocks: A Comparison Between the Flap and Tunneling Procedures"; 2014 American Association of Oral and Maxillofacial Surgeons; J Oral Maxillofac Surg 72:1660-1670, 2014.

John N. Kent, DDS, et al.; "Alveolar Ridge Augmentation Using Nonresorbable Hydroxylapatite with or without Autogenous Cancellous Bone"; J. Oral Maxillofac Surg, 41:629-642; 1983.

Carlo Mazzocco, MD, DDS, et al.; "The Tunnel Technique: A Different Approach to Block Grafting Procedures"; The International Journal of Periodontics & Restorative Dentistry; vol. 28, pp. 44-53, No. 1, 2008; Quintessence Publishing Co, Inc., © 2008.

Ernesto A. Lee, DMD, et al.; "Lingualized Flapless Implant Placement into Fresh Extraction Sockets Preserves Buccal Aveolar Bone: A Cone Beam Computed Tomography Study"; The International Journal of Periodontics & Restorative Dentistry; vol. 34, pp. 60-68, No. 1, 2014; Quintessence Publishing Co, Inc. © 2014.

Marc I. Nevins, DMD, MMSc et al.; "Minimally Invasive Alveolar Ridge Augmentation Procedure (Tunneling Technique) Using rhPDGF-BB in Combination with Three Matrices A case Series", The International journal of Periodontics & Restorative Dentistry, vol. 29, No. 4, 370-385, 2009, Quintessence Publishing Co. Inc.

* cited by examiner

SUBPERIOSTEAL SYRINGE DEVICE FOR ADMITTING BONE GRAFT MATERIAL INTO A SUBPERIOSTEAL LOCUS

BACKGROUND OF THE INVENTION

1. Field of the Invention

The present invention relates to devices and systems for storing and delivering bone material and one or more growth substances, and in particular granular bone particles or paste, and a growth factor to a subperiosteal location through a tunnel in the tissue of a patient.

2. Brief Description of the Related Art

Dental implants are widely used to replace lost or damaged teeth. In order for implants to be successfully installed, there must be suitable bone structure for the implant to attach to. Although technically the "implant" denotes the structure that replaces the tooth roots and provides the foundation for synthetic teeth, it is sometimes used interchangeably also to refer to the teeth. Implants typically consist of a titanium screw or post that is secured within a location of the jaw bone. Surgical techniques routinely involve making or refining a hole in the jaw bone and securing the implant in the hole. Often the implant is secured with the gum tissue and bone that grow around the implant site.

Tooth damage may coincide with bone defects in the human maxilla. For example, there may be premature loss of teeth as a result of periodontal disease or other disruption or trauma. In instances where there is a reduction is alveolar bone volume, bone reconstruction, which may involve augmentation of the existing bone, is often required. Augmentation procedures involve surgical incisions made into the tissue around the jaw, and placement of bone material, also referred to as a graft, at a desired site that will strengthen the implant. In order to introduce bone graft material to the location, prior methods have involved making an incision to expose an area of the bone by separating flaps of tissue, depositing the bone material in the exposed area, and closing the incision to secure the bone graft at the location within the tissue. Bone particles are often administered together with a growth factor to promote attachment of the bone to existing bone and the surrounding tissue. Current methods involve utilization of a spatula or tool to position the bone graft material in the incision location.

The aging process results in changes to the skin and facial structures that will result in wrinkles, skins, and concavities from lack of support of the facial soft tissues. The implantation of a non-resorbable or slow-resorbing bone grafting material into a subperiosteal locus may help in providing support for the lips, cheeks, note, chin, and other facial tissues, thereby enhancing facial esthetics. A device that allows the delivery of the bone graft material using a subperiosteal intraoral approach is advantageous in avoiding dermal scars.

A need exists for a device that facilitates introduction of bone graft material into a reconstruction site, and in particular, a device that may be inserted and maneuvered within the tissue to deliver bone graft material to a desired location without the need to expose the patient's bone.

SUMMARY OF THE INVENTION

A subperiosteal syringe device is provided for facilitating the delivery of bone to a location within the tissue of a jaw, face or elsewhere within the body and, in particular, the delivery of particulate bone graft material that is comprised of bone particles, and preferably a growth factor, but may also include paste and gel like materials which, for example, may contain collagen, and binding or adhesive agents. The device is constructed so that a user may position the device within the subperiosteal tissue, and at a desired location within the subperiosteal tissue to deposit the particulate bone graft material. The device is configured to be used inside a subperiosteal tunnel. According to preferred embodiments, the device is configured having a lumen body with an actuator, such as a plunger, that is moved within the lumen body to expel the bone graft material from an end of the device. The device configuration preferably comprises a subperiosteal syringe designed for use inside a subperiosteal tunnel. The device may be used as a carrier to deliver particulate bone graft material to a location inside the subperiosteal tissue, and more particularly, to a surgical site, such as a subperiosteal pouch that is reachable through a subperiosteal tunnel.

According to some embodiments, the subperiosteal syringe device includes a lumen body portion into which bone graft material to be delivered to the surgical site is placed. The bone graft material, for example, may comprise granular bone particles or a bone substitute in paste form, and agents, such as growth factors, binding or adhesive substances. According to some embodiments, the syringe may be preloaded with bone particles, and, in some embodiments, the pre-loaded bone graft material also may include an agent, such as a growth factor, collagen, adhesive and binding agents.

According to some alternate embodiments, the device is constructed to contain bone particles, within the lumen body, or a paste containing bone particles, and to also include a means for admitting a substance, such as a growth factor or a catalyst, into the lumen where the bone particles are stored. In the device embodiments with this feature, the bone particles may be preloaded into the lumen without an agent, such as a growth factor, and, when the bone particles are ready to be used (i.e., ready for placement at the patient site), the growth factor is admitted into the device lumen. Another preferred embodiment includes admitting a catalyst that will cause the setting of a biphasic material or paste into a solid or semisolid form. According to some embodiments, a means for admitting a substance to the lumen may comprise a cap fitted on the open end of the device that may be punctured, for example, with a needle of a syringe, to introduce a liquid substance into the lumen. According to some embodiments, the syringe may be preloaded with a granular bone substitute pretreated with a biologic agent or growth factor. According to alternate embodiments, the syringe may be loaded with granular or paste like material, and may be combined with collagen. According to alternate embodiments, the syringe may include an automatic mixing design to be used with biphasic materials, whereby a base and catalyst are combined to trigger a chemical or physicochemical reaction.

According to preferred embodiments, the device is configured as a subperiosteal syringe, and is constructed to be insertable within a passageway that has been surgically created in the jaw or facial tissues. For example, the passageway may include a path or tunnel surrounded by tissue, and may lead to an area where the bone material is desired to be deposited. Preferably, the device includes an end portion designed to guide the lumen (e.g., through a tunnel developed in the tissue) that projects forward relative to a trailing portion of the lumen. The forward projecting end portion effects a gradual raising of the tissue, such as the mucosa and periosteum, that forms the tunnel as the lumen is inserted into the tunnel, and moved within the tunnel. According to some embodiments, the lumen end is beveled at the delivery end to form a beveled opening, where a portion of the lumen wall having a thickness of the lumen wall, forms a leading edge. The device preferably includes a plunger which, when actuated, is moved through the lumen body to expel the contents from the device out through the beveled opening. According to some preferred embodiments, the device lumen body is configured to hold a discrete amount of bone graft material, and the plunger is provided to travel a suitable length of the device to deliver a suitable amount of bone graft material.

The syringes may be configured according to some embodiments, to provide a beveled opening which has a curved or radial profile. For example, the curve may be uniformly provided, or may have one or more sections of curvature that have a different arc profile than one or more other sections. The leading portion of the syringe also may be provided with an inwardly tapered end, which, for example, may taper toward the syringe longitudinal axis. The taper for example, may begin at the location opposite the trailing edge opening, and may taper to the syringe end. The bevel profile may be straight, or may be curved, so that the tapered leading portion may be provided in a number of embodiments. According to some embodiments, the leading portion of the syringe may be configured with a wide or broader configuration to facilitate lifting of the mucosa and the periosteum, as the syringe is passed through a remote incision and maneuvered through a subperiosteal tunnel.

The device may include markings along the lumen body to denote the amount (e.g., volume, cc's, and the like) of material dispensed from or present within the syringe lumen. The syringe device may include markings thereon that identify the depth of insertion of the device when the device lumen has been inserted within the patient's tissue (e.g., such as within a subperiosteal tunnel). Markings may be used to identify penetration depth, and, for example, according to some embodiments, may be provided as increasing depth numbers as the distance from the beveled delivery end increases. The sets of markings, such as the content volume markings, and depth markings, preferably are provided along two different locations of the lumen (such as, for example on opposite longitudinal sides).

Preferred embodiments of the device may be configured having a non-cylindrical shape lumen, which according to some embodiments may comprise a flattened hollow structure (e.g., such as a flattened tube). Some examples of non-cylindrical shapes include oval or elliptical shaped lumens. According to some embodiments, the subperiosteal syringe device may have a lumen body with a flat side spanning along one side of its length, and with a curved or arcuate shape spanning along the other side. The device flat side provides assistance for placement of the device along the bone, while the curved profile on the opposite side length facilitates passage of the device through the tissue, and preferably, reduces restriction during insertion as the curved surfaces engage the tissue. According to some embodiments, the subperiosteal syringe may be constructed having a curved or radial body, which preferably may be curved to correspond with the geometry of a jaw curvature to facilitate maneuverability within a curved tunnel path of the periosteum.

The subperiosteal syringe device preferably is maneuverable through the periosteum, and in particular through a subperiosteal tunnel. The configuration of the syringe is designed to minimize or eliminate impingement on the mucosa, while allowing subperiosteal maneuverability.

The subperiosteal syringe is configured so that it is easy to load with bone particles and may accept introduction of an additional substance, subsequent to or in combination with the loading of the bone particles. According to some embodiments, the subperiosteal syringes may be provided empty, and may be loaded with bone particles or paste material and a growth factor by the end user. This may be done by syringing the bone graft material and growth factor into the lumen by withdrawing the plunger. Alternatively, the bone graft material and growth factor may be loaded into the open end of the subperiosteal syringe, together, or separately.

Alternatively, the subperiosteal syringe may be preloaded with bone graft material, and supplied to the end users with the bone graft material in the desired particle size, paste or composition.

Subperiosteal syringes according to the invention are configured to receive bone particles therein, and are provided with a sealing mechanism to seal the bone particles within the syringe interior. The subperiosteal syringes include a feature that permits a liquid substance to be admitted to bone particles that are situated within the lumen. Subperiosteal syringes according to the invention may be provided pre-loaded with a predetermined amount of particulate, paste, or gel bone material (e.g., by weight, volume, particle size, density, and/or the like), and may be shipped and stored with the bone particles therein. The bone particles may be pre-treated. According to some embodiments, where it is preferable to introduce an additional treatment agent to the bone particles at the time of their use (such as a growth factor), the agent or growth factor may be supplied in the form of a liquid and admitted to the syringe interior (where the bone particles are present). According to a preferred embodiment, a protective cap is provided to cover the syringe opening. The end cap preferably is constructed from a material that is puncturable. The bone graft material may be supplied preloaded within the syringe lumen body and remains sealed therein from contaminants, with the plunger head sealing one end of the lumen and the end cap sealing the other lumen end. The end cap is constructed to permit passage of a needle therethrough, preferably by a puncture, so that a substance, such as a growth factor, may be administered to the interior of the syringe, e.g., to the bone particles.

Preferably, the subperiosteal syringe is constructed to minimize or prevent the separation of its component parts, fractures and/or shearing when the device is in use. For example, some preferred embodiments may provide a monolithic plunger, which includes a plunger head, shaft and actuation end. The syringe lumen body preferably is constructed from a material that is rigid but permits some flexibility. According to some preferred embodiments, plastic material may be used to construct the lumen body. The plunger may be formed from a rubber, silicone, or other suitable material that is capable of providing a seal against the lumen body interior.

One or more of the features discussed herein, including those discussed above, may be provided separately or together with one or more other features in subperiosteal syringes according to the invention. These and other advantages may be provided by the inventive devices shown and described herein.

BRIEF DESCRIPTION OF THE DRAWING FIGURES

DETAILED DESCRIPTION OF THE PREFERRED EMBODIMENTS

A subperiosteal syringe device for delivering bone graft material to a location within the tissue of a jaw, the face, or other bones, and, more particularly, for delivering the bone graft material via insertion of the device within a tunnel that has been surgically developed in the subperiosteum of a patient. The device is useful for carrying out subperiosteal jaw and facial augmentation or reconstruction procedures. In particular, the subperiosteal syringe is configured for carrying out procedures where the surgical site remains hidden from view and is reachable through a tunnel within the jaw tissue that has an opening remote from the surgical site (where the bone graft is to be implanted), and where the tunnel leads to the surgical site. The subperiosteal syringe device is maneuverable within the subperiosteal tissue (e.g., through a surgically developed tunnel) to a desired location within the tissue adjacent the bone to be augmented or reconstructed. When the device is positioned at a desired location (e.g., where the device opening is at the surgical site or pouch to receive the implant), the device contents, such as bone graft material that contains bone particles, may be delivered to the site.

According to some embodiments, the syringe may be used for carrying out bone augmentation applications, with our without subsequent or concomitant implant placement, where the graft material is placed directly over bone, and under the periosteum. The syringe also may be used to carry out bone graft delivery according to another embodiment, where bone graft material is added to treat implants that are lacking bone. In this latter application, the lack of bone at an implant may be a result of improper placement, or bone loss that has taken place over the years.

Figure 1A:
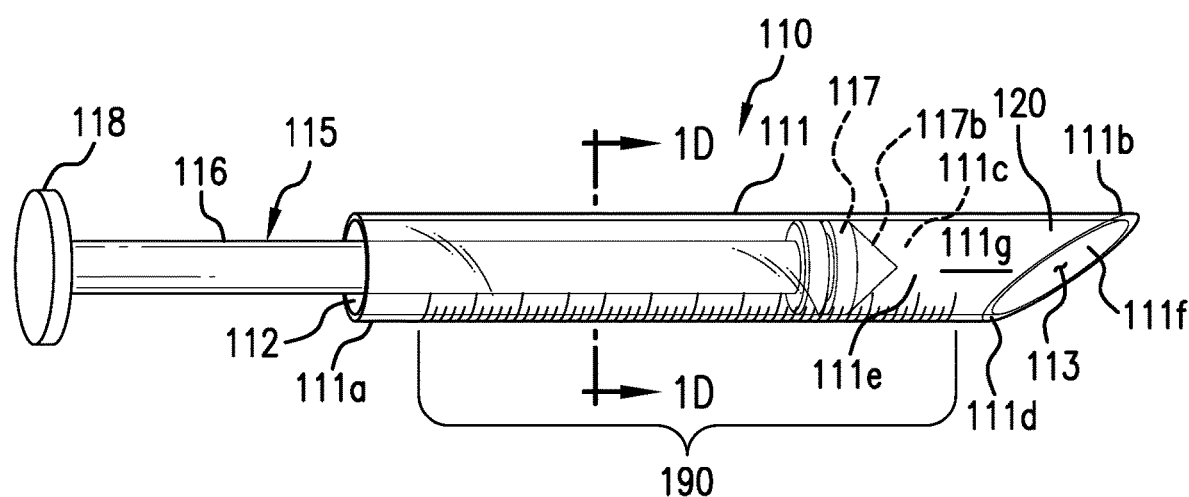
FIG. 1A is a right side perspective view of a first embodiment of a subperiosteal syringe device according to the invention.
Figure 1B:
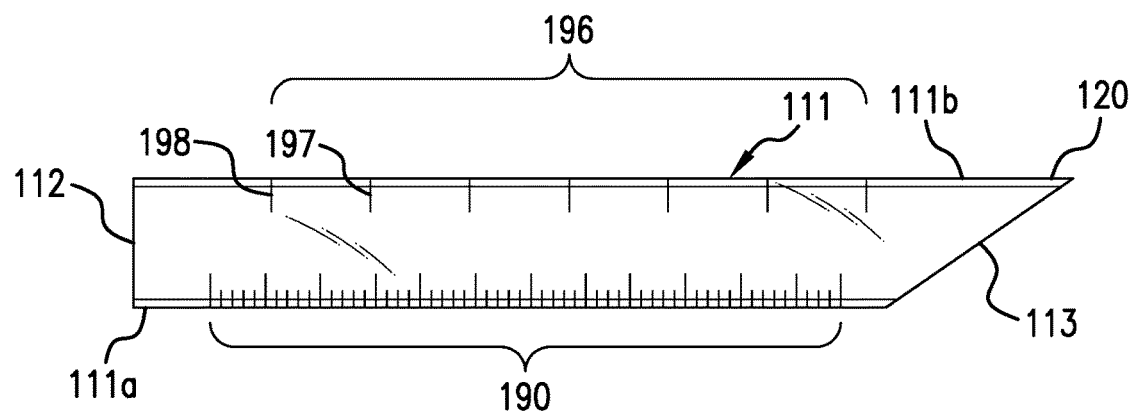
FIG. 1B is a perspective of the subperiosteal syringe device of FIG. 1A, as viewed looking from the right side, and showing the lumen body separate from the plunger.
Figure 1C:
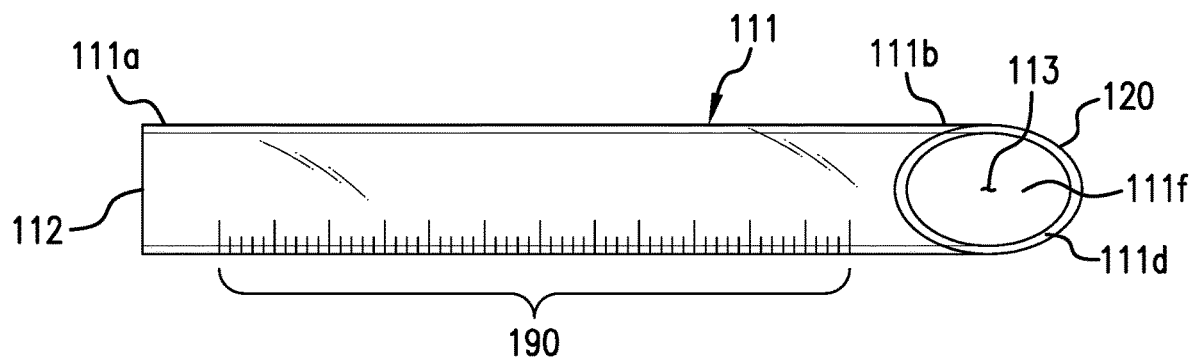
FIG. 1C is an enlarged perspective view of the bottom of the lumen body shown in FIG. 1B.
Figure 1D:
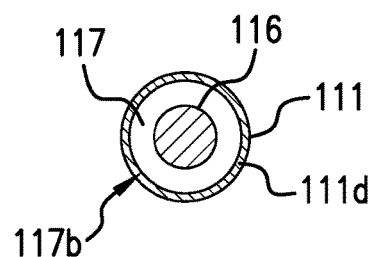
FIG. 1D is a sectional view of the plunger of the device of FIG. 1A shown separately from the lumen, the section being taken above the plunger head and looking down the plunger shaft.

Referring to FIGS. 1A-1C, there is illustrated a first exemplary embodiment of a subperiosteal syringe device 110 for delivering bone graft material to a subperiosteal site. According to the exemplary embodiment, the subperiosteal syringe device 110 has a body comprising a lumen 111 with a first opening 112 at one end 111a thereof and a second opening 113 at the opposite end 111b thereof. The lumen 111 defines a cavity 111c therein. Preferably, the lumen 111 has a thickness 111d, defined by the lumen wall 111e. The lumen wall 111e includes an interior surface 111f and an exterior surface 111g.

The syringe assembly 110 is shown including a plunger 115 with a shaft 116 and a head 117. The plunger head 117 is sized to fit within the lumen cavity 111c and sealingly engages the lumen interior wall 111f. According to preferred embodiments, as illustrated in FIG. 1A, an actuator 118 is associated with the plunger 115, and in the embodiment illustrated, the actuator 118 is provided as part of the plunger 115. The actuator 118 is designed to be manually controlled to move the plunger 115 and plunger head 117 along the lumen 111 and through the lumen passageway 111c. The plunger head 117 preferably fits tight against the lumen body wall 111e, and in particular the interior wall 111f, making an airtight seal. Preferably the seal seals air, humidity and potential contaminants from entering into the syringe body cavity 111c. Movement of the actuator 118 causes the plunger shaft 116 and head 117 to slide through the lumen 111 and express the syringe contents out from the second opening 113, which is the delivery opening. Preferably, the subperiosteal syringe 110 is loaded with bone graft material 200 (see FIG. 2) which is contained within the lumen body 111 out from which it is delivered via the syringe opening 113 to express the bone graft material at a surgical site. The subperiosteal syringe 110 may be loaded using a suitable method, including syringing the bone graft material into the opening 113 at the end 111b, for example, to take up the bone graft material and any substance that is may be mixed with it (such as a growth factor).

Figure 2:
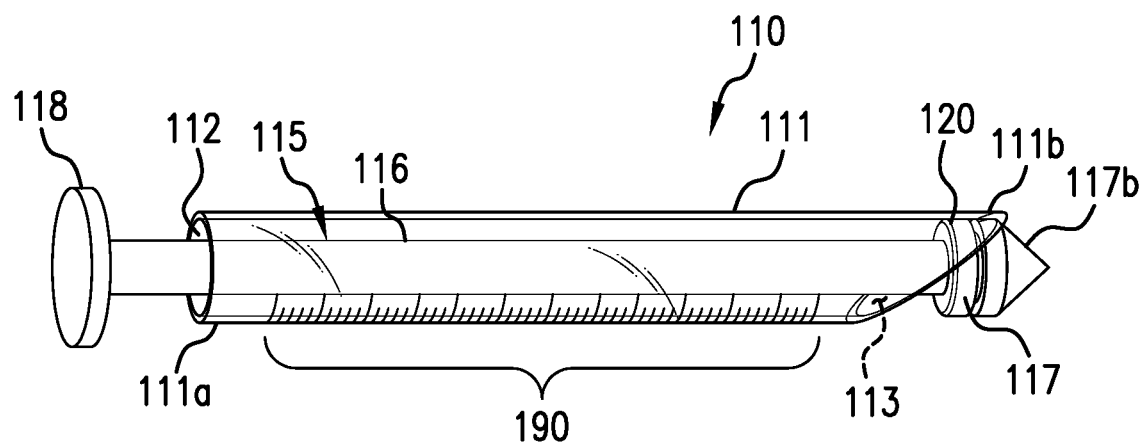
FIG. 2 is a right side view of the device of FIG. 1, shown with the plunger in a position where it is extending through the body.

As depicted in FIG. 1A, the plunger 115 is configured to have a suitable length to express a desired amount of material from the syringe 110. According to the exemplary embodiments, as depicted in FIG. 2, the plunger 115 may travel through the lumen opening 111c a predetermined distance so as to dispense a predetermined amount of bone graft material. The bone graft material may be provided preloaded within the syringe 110. The syringe 110 may be configured to accept and store a predetermined amount of bone graft material in its cavity 111c until it is needed for a procedure.

The syringe 110 preferably includes a means for admitting a material to the bone particles that are present within the syringe. Preferably, the means for admitting material comprises a mechanism for introducing a liquid material into the lumen cavity 111c where the bone particles are present.

Figure 5:
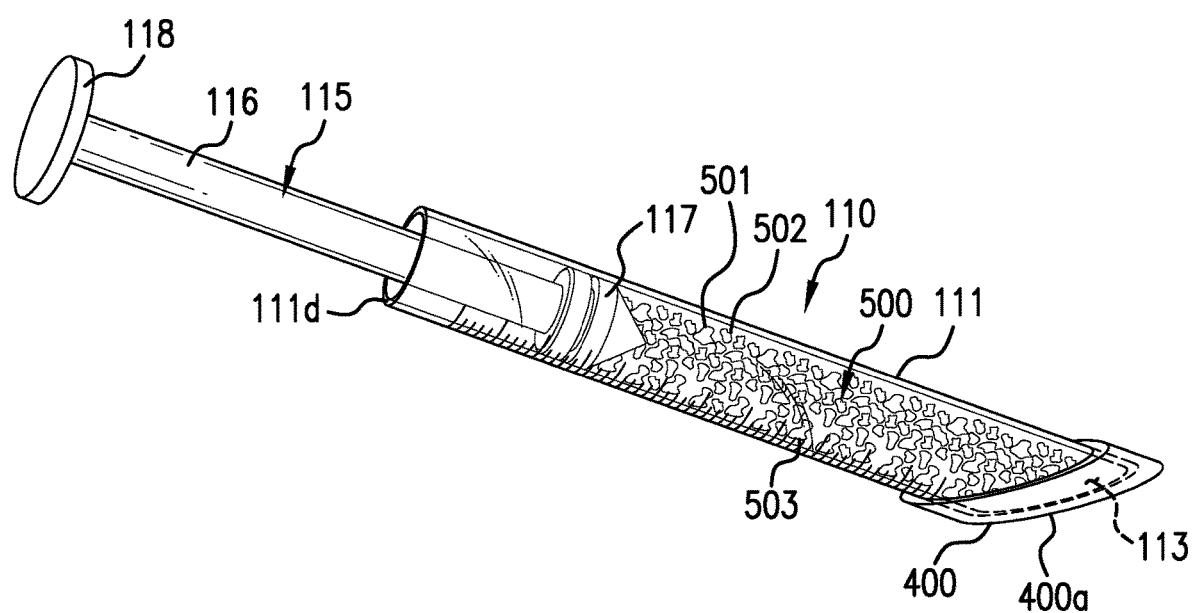
FIG. 5 is a right side view of the first embodiment of the subperiosteal syringe device of FIG. 1A, shown with the end in perspective view to illustrate the opening.

As illustrated in the exemplary embodiment of FIG. 5, the mechanism is configured to comprise an end cap 400, which is made from a material that may be punctured with a needle. The end cap 400 is configured to secure material (e.g., bone particles) within the lumen body 111 by making a tight seal against the lumen 111. The end cap is shown provided to cover the lumen opening 113, and may form a tight fit on the lumen end 111b. The end cap 400, or at least a puncturable portion thereof, is made from a material that may be punctured with a needle. The needle may be attached to a separate syringe (not shown), which may be loaded with a suitable agent, such as a growth factor. The liquid, such as the growth factor, is delivered through the end cap 400 and into the lumen cavity 111c, and, in particular, is administered to the bone particles residing in the lumen 111. The end cap 400, or puncturable portion thereof, such as for example, the central area 400a, is constructed from a material that is designed to receive the needle puncture therethrough, and, upon the withdrawal of the needle from the end cap 400, is designed to close the puncture opening made by the needle. The end cap may be puncturable across its entire surface, or alternatively, may have a preferred puncture area, such as, for example, the designated area 400a. Although not shown, the end cap 400 may be provided with a groove or other suitable structure, such as an indentation, a colored or dotted area, to facilitate the direction of the needle therethrough. According to some embodiments, the puncture area is configured to guide the needle and may provide a path or guide (not shown), for facilitating insertion of the needle through the end cap 400.

Similarly, the end cap 400 although illustrated in connection with a cylindrical lumen in FIG. 5, preferably is constructed to fit over other lumen openings, such as where the lumen is configured with a flattened, elliptical, or has a flat side.

In the embodiment illustrated in FIG. 1A, the lumen body 111 is depicted having a substantially cylindrical shape. According to preferred embodiments, the plunger 115 is sized to pass entirely through the lumen body 111. Referring to FIG. 2, the plunger 115 is illustrated in a position within the lumen 111, where the plunger 115 has traveled a length to where it will have expressed the contents out of the subperiosteal syringe 110. According to preferred embodiments, the plunger head 117 may have a tapering end portion 117b which is the leading portion. The plunger end portion 117b, for example, is shown being tapered, and illustrated having a conical shape. According to preferred embodiments, the plunger head is configured to comprise a structure that serves to break up agglomerations of bone particles and to prevent compaction of the particles within the syringe lumen. In the exemplary embodiment illustrated, the plunger head 117 is shown having a pointed tip, which is designed to break up agglomerated bone particles.

According to preferred embodiments, the syringes 110, 210, 310, etc., preferably have markings on the body to designate one or the other or both of the lumen content volume and the penetration depth of the subperiosteal syringe. The markings 190 preferably identify a measure of the volume of the contents, and the plunger position relative to one of the marking lines provides an indication of the volume of bone graft material, for example, to determine an amount delivered, or an amount remaining to be delivered. The markings 190 preferably may be provided with numerals (not shown) that increase in the direction toward the actuator end 111a of the lumen 111 (i.e., a direction away from the delivery end 111b). The depth markings 196 (FIG. 1B) may denote an end depth, which preferably may signify the distance D to the lumen body end 111b, which denotes the depth that the lumen has been inserted. For example, where the syringe 110 is inserted into a subperiosteal tunnel, the syringe lumen body 111 typically will be out of the sight of the user. The markings 196 preferably may be provided with numerals (not shown) that increase in the direction toward the actuator end 111a of the lumen 111 (a direction away from the delivery end 111b). For example, where an indication at the marking line 197 is provided, it may for example, represent 7 cm insertion depth, and be marked with a numeral "7" or "7 cm" so that when the syringe 110 is positioned within a subperiosteal opening, such as a tunnel in the patient's jaw tissue, the depth of the inserted portion is identifiable by the marking 197. For example, where the syringe 110 is inserted an additional amount, such as, for example, an additional 1 cm, then, the marking line 198 will represent 8 cm, and may be provided to bear a marking, e.g., "8" or "8 cm", to identify that the insertion depth is 8 cm. Although numerals and units have been omitted from the figures for clarity in presenting the syringe, the syringe body 111 markings, such as those 190 and 196, may be marked with respective corresponding markings that include numbers and units. In addition the cm lengths discussed herein are to illustrate an example of measurement, and the subperiosteal syringes of the invention may be made shorter or longer as desired.

The subperiosteal syringe device includes a portion designed to guide the lumen (e.g., through a tunnel developed in the tissue) which comprises a leading portion of the lumen at the delivery end 111b. As illustrated in FIG. 1A, the leading portion 120 projects forward relative to a trailing portion of the lumen 121. The forward projecting portion 120 effects a gradual raising or elevation of the tissue forming a subperiosteal tunnel into which the subperiosteal syringe lumen 111 is to be inserted. The projecting portion 120 of the device 110 preferably is used to elevate the mucosa, providing entry of the syringe lumen 111 into the tunnel and facilitating movement therethrough. The projecting portion 120 preferably is configured as an extension of the lumen 120, and in the embodiment illustrated, forms a projection above a portion of the lumen cavity, with the underside of the projection being open. The projecting lumen portion 120 aids to deliver the bone graft material from the syringe lumen to the desired location by directing the bone graft material as it is being expressed toward the bone side of the surgical site (below the projection 120), and preferably to the bone surface.

According to some embodiments, the projection 120 may be formed by producing a bevel in the lumen end 111b. The lumen end 111b is beveled at the delivery end to form a beveled opening 113, where a portion of the lumen wall having a thickness of the lumen wall, forms a leading edge. As illustrated in FIG. 1A, the syringe 110 delivery end opening 113 is configured to comprise a beveled opening 113a. The beveled opening 113a is formed by a first portion of the lumen 111 that extends beyond a second portion of the lumen 111. The longitudinal length of the lumen 111 is illustrated having a bevel that is depicted being disposed at about 45 degrees, although other bevel angles are possible. The bevel at the end of the syringe 110 is provided to face the bone surface (so that the extended portion of the lumen is opposite the bone surface), for example, when the syringe 110 is used to deliver bone graft material to a patient.

Figure 3A:
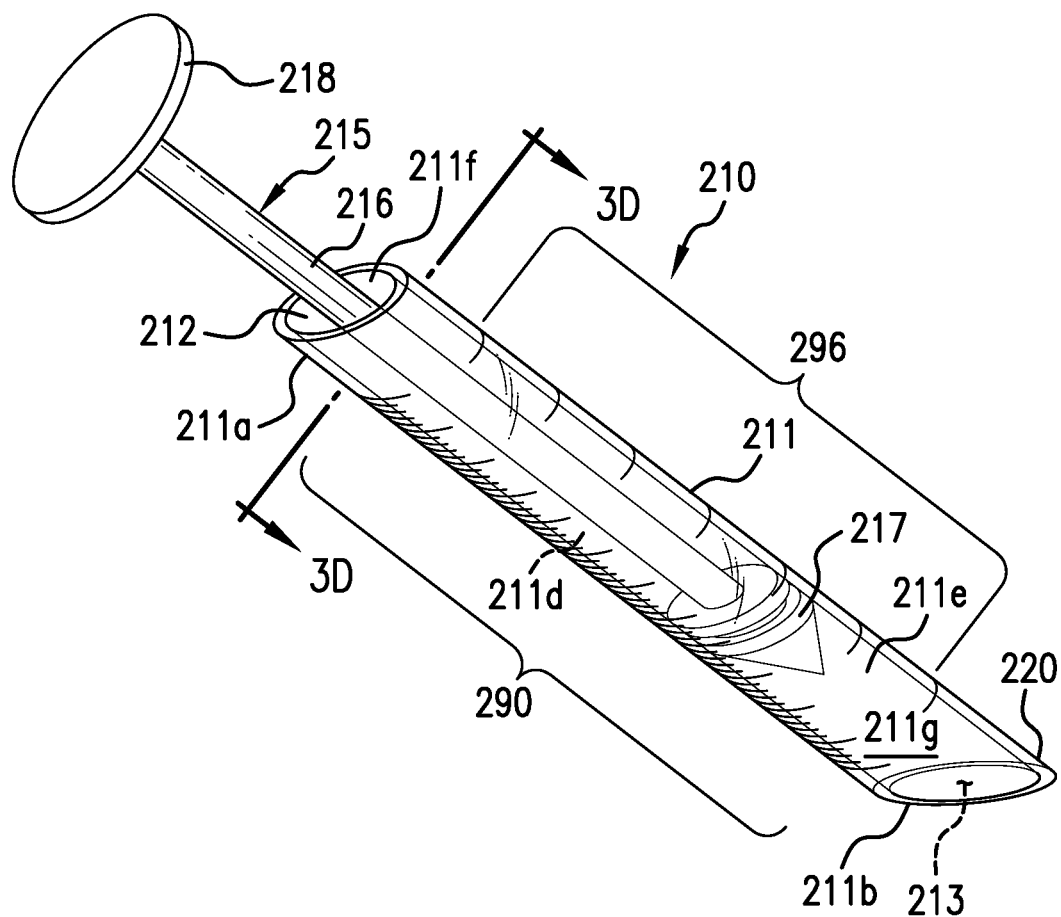
FIG. 3A is a perspective of a second embodiment of a subperiosteal syringe device according to the invention, as viewed looking from the right side.
Figure 3B:
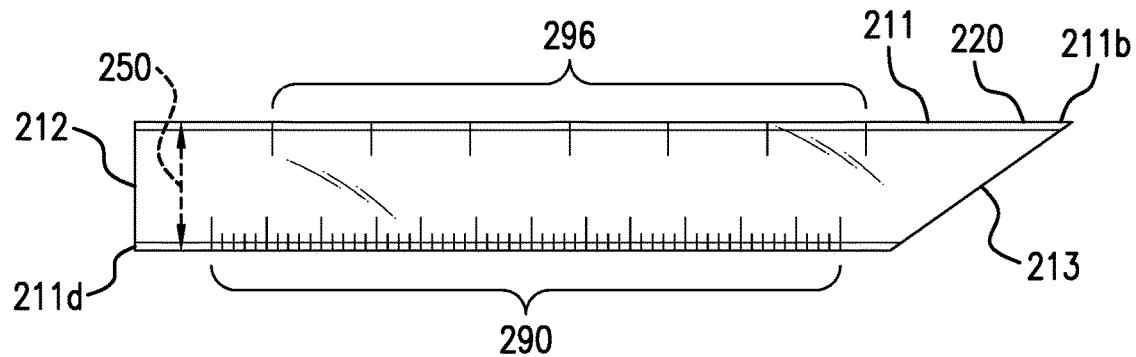
FIG. 3B is a perspective view of the bottom of the second embodiment of the subperiosteal syringe device shown in FIG. 3A.
Figure 3C:
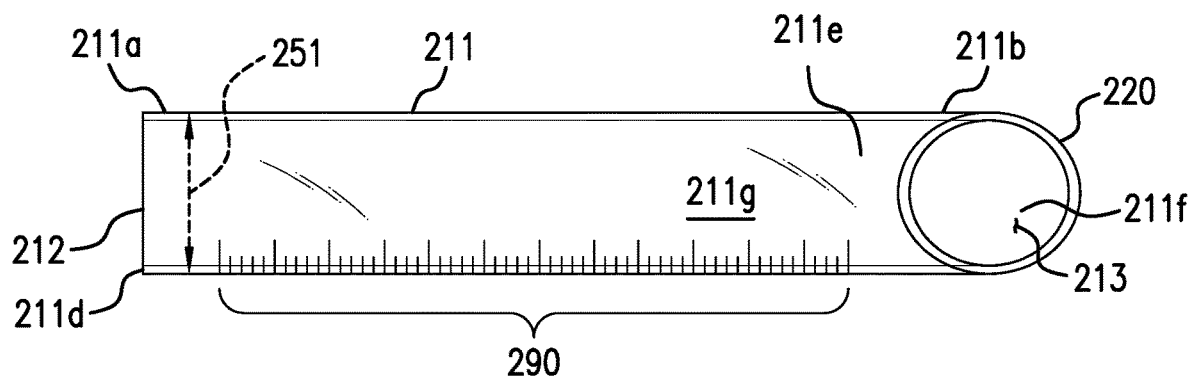
FIG. 3C is a sectional view of the plunger of the device of FIG. 3A shown separately from the lumen, the section being taken above the plunger head and looking down the plunger shaft.
Figure 3D:
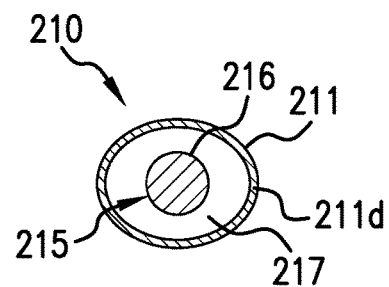
FIG. 3D is a sectional view of the plunger of the device of FIG. 3A shown separately from the lumen, the section being taken above the plunger head and looking down the plunger shaft.

Embodiments of the syringes shown and described herein may be configured with configurations that facilitate insertion and maneuverability within the tissue of a patient, such as, for example, a subperiosteal tunnel through which bone graft material is to be delivered to an ultimate surgical site accessible through the tunnel. Referring to FIGS. 3A-3C, according to an alternate embodiment, a subperiosteal syringe 210 is depicted having a lumen 211 that is non-cylindrical. In the embodiment illustrated in FIG. 3, the syringe lumen 211 is shown having an elliptical configuration. The lumen 211 has a first opening 212 at one end 211a thereof, a second opening 213 at the opposite end 211b thereof, and a cavity 211c therein. 211d, an interior surface 211f, and an exterior surface 211g. The lumen cavity 211c is elliptical in cross-section (see FIG. 3D). According to preferred embodiments, the cross-sectional shape of the cavity 211c matches the shape of the syringe body lumen 211, and preferably, the shape of the exterior surface 211g. A projection of the lumen leading portion 220 is provided at the delivery end 211b. According to a preferred embodiment, a beveled opening 213a is formed by the projection 220. The projection 220 is shown comprising an extended portion 211h of the lumen 211. The extended portion 211h preferably is comprised of the wider arc of the ellipse, so that the elliptical body 211 has a broader portion of the lumen end 211h forming the beveled opening 213a. The cross-sectional view of FIG. 3D illustrates a preferred configuration with the lumen projecting end 220 being shown.

A plunger 215 is provided to fit within the lumen cavity 211c. Preferably, the profile of the plunger head 217 corresponds with the elliptical profile of the lumen interior wall 211f. The plunger 215 may be constructed with a plunger head 217, and plunger shaft 216 as described and illustrated in connection with the subperiosteal syringe 110, and the plunger 115. The plunger 215, shaft 216, and plunger head 217 preferably are constructed from a material as described in connection with the plunger 215. As discussed above, in accordance with preferred embodiments, the plunger 215 may be a monolithic structure comprising an actuator 218, shaft 216, and head 217. The plunger head 217 preferably has a leading edge or tip end that may be tapered, such as the conical end 217a, to facilitate expulsion of the syringe contents at a desired rate. The plunger head 217 or portion of the head in sealing contact with the lumen interior wall 211f, preferably is elliptically shaped, and may taper from an elliptical profile (where it is in contact with the lumen interior wall) to the leading end of the head 217 which may be formed by a tapering wedge or elliptical converging end. The head 217, as well as the plunger head 117, may be provided with rounded or softened edges at the trailing end, so that when the plunger head 217 (and head 117) travels beyond the lumen opening 213 (and 113, as shown in FIG. 2), retracting the syringe 210 from the tunnel will minimize impingement on the surrounding tissue.

According to alternate embodiments, the lumen of a syringe according to the invention may comprise a longitudinal length with at least one portion, such as a first portion, of the longitudinal length spanning in a longitudinal direction, and at least one other portion, such as a second portion, of the longitudinal length spanning in a longitudinal direction. The first portion and second portion preferably are parallel to each other. According to some embodiments, the first portion and the second portion may be disposed on opposite longitudinal sides of the lumen. Embodiments may be constructed so that at least one of the portions extends longitudinally beyond the other portion to form the lumen opening that will express the bone graft material, as well as to provide a leading portion to facilitate opening of the tunnel for the portions of the lumen that trail the leading portion. The opening formed from the first portion and second portion may comprise a beveled opening. Referring to FIGS. 4A-4D, a third alternate embodiment of a device 310 according to the invention is illustrated, and includes a first portion configured to have one shape and a second portion configured to have a second shape. The subperiosteal syringe device 310 has a body or lumen 311. The lumen 311 has a first opening 312 at one end 311a thereof, a second opening 313 at the opposite end 311b thereof, and a cavity 311c therein. The lumen wall has a wall thickness 311d which preferably represents the thickness of the lumen wall first portion 311e and lumen wall second portion 311f. The lumen wall portions 311e, 311f preferably are constructed together to form a lumen 311 comprising a first portion 311e and second portion 311f. In the embodiment depicted, the lumen 311 is constructed to have a non-uniform configuration. In the embodiment illustrated in FIGS. 4A and 4B, the lumen 311 is shown having a substantially flat portion 311f spanning its longitudinal length and forming the shorter side of the lumen at the lumen opening 313. According to preferred embodiments, the subperiosteal syringes according to the invention may be constructed with a flat portion, which preferably spans the length of the lumen, and on one longitudinal side thereof, as shown in the exemplary depiction of the syringe body or lumen 311 of FIGS. 4A and 4B. The flat portion 311f of the syringe 310 is provided to be used against the bone surface (of existing bone of a patient).

Figure 4A:
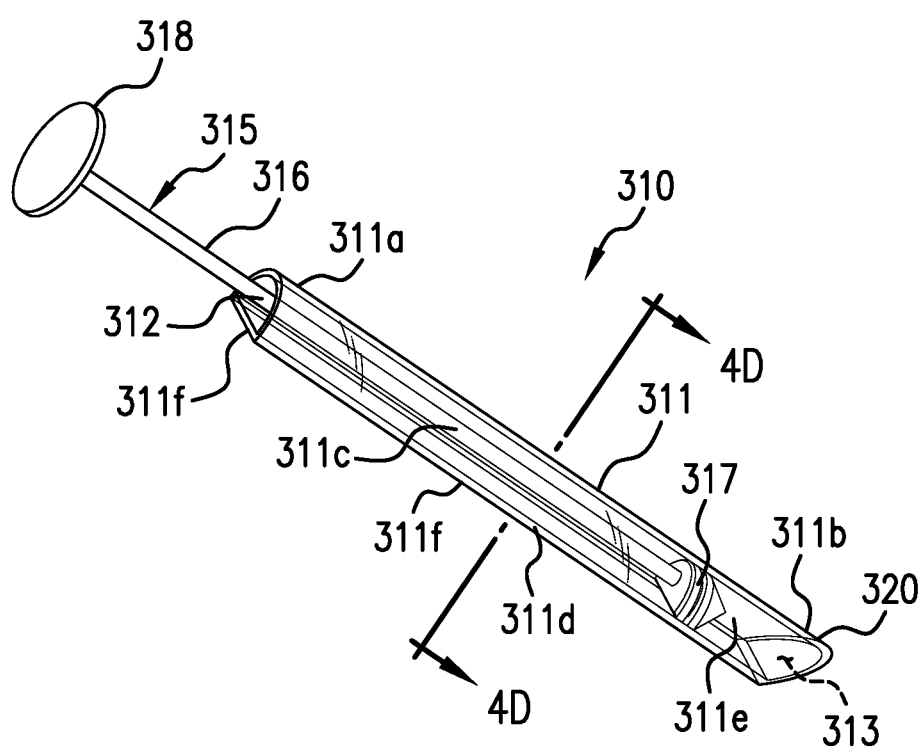
FIG. 4A is a perspective of a third embodiment of a subperiosteal syringe device according to the invention, as viewed looking from the right side.
Figure 4B:
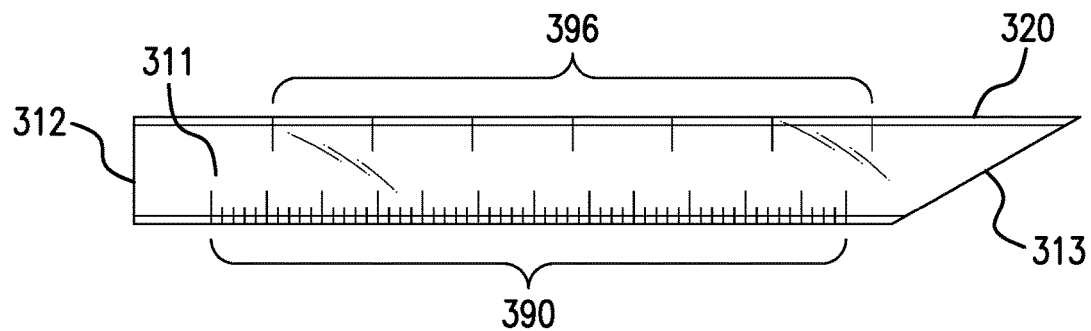
FIG. 4B is a perspective view of the bottom of the second embodiment of the subperiosteal syringe device shown in FIG. 4A.

In the embodiment depicted in FIGS. 4A and 4B, the lumen 311 is shown having a second portion 313e that spans a longitudinal length which forms the leading portion 320 of the lumen 311 that defines the front of the bevel opening 313. The second portion 313e preferably comprises a portion that is not flat, and which preferably has a curved, radial or other type of arcuate configuration. In the embodiment illustrated in FIG. 4, the non-flat portion is shown having an elliptical configuration formed by the elliptical wall portion 311e. Bone material is expressed from the syringe opening 313 and the protruding portion, which in the syringe 310 is the leading portion 320 of the curved wall portion 311e.

Figure 4C:
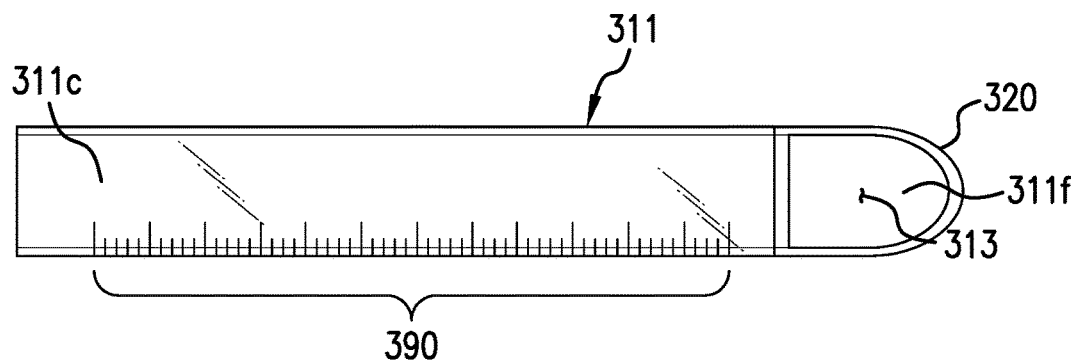
FIG. 4C is a sectional view of the plunger of the device of FIG. 4A shown separately from the lumen, the section being taken above the plunger head and looking down the plunger shaft.
Figure 4D:
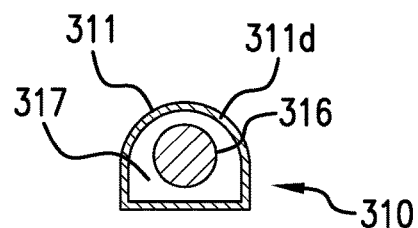
FIG. 4D is a sectional view of the plunger of the device of FIG. 4A shown separately from the lumen, the section being taken above the plunger head and looking down the plunger shaft.

As shown in FIG. 4C, the syringe 310 preferably includes a plunger 315 with a shaft 316, an actuator 318 and a plunger head 317 with a profile corresponding to the inner wall portions of the lumen 311. The syringe plunger 315 preferably may be constructed similar to those plungers 115, 215 shown and described herein, to allow introduction via a syringe needle of a liquid (e.g., growth factor) into the cavity 311c where the bone graft material is held. The plunger head 317 includes a first plunger head portion that is a flat portion, and a second plunger head portion that is curved. The plunger head 317 preferably is configured with a profile that matches the interior wall structures of the lumen 311. According to some alternate embodiments, the lumen wall thickness may be provided with rounded edges along the lengths where the interior wall first portion meets with the second portion. This may be done to provide the plunger with a curved profile at the edges. The lumen exterior may include the curved edges, or may provide more discrete edges that are different than curved edges that may be provided long the interior of the lumen (where the interior wall first and second portions join). In this latter instance, the thickness of the lumen wall may be increased along those longitudinal edges where the first portion meets with the second portion.

Referring to FIG. 5, the circular embodiment of the subperiosteal syringe 110 of FIG. 2 is shown loaded with bone graft material 500 comprising bone particles (501, 502, 503, et seq. . . . ) disposed within the lumen cavity 111c of the syringe 110. The syringe 110 is depicted in an embodiment where it is pre-loaded with bone graft material 500. The bone graft material 500 may comprise treated or untreated material. For example, the bone graft material 500 may comprise bone graft particles (501, 502, 503) that are treated with a treatment agent, such as, for example, a growth factor. Alternate embodiments may provide the bone graft material in the form of bone particles which have not been treated, or, if they have been previously treated (at the time of or prior to loading the bone material in the syringe), require further treatment with a substance, such as, for example, a growth factor, or a biologic adhesive or binding agent. Additional alternative embodiments may provide a graft material in the form of a paste, or in combination with collagen, both of which may be treated or untreated with a biologic agent such as a growth factor, biologic adhesive or binding substance; or to which a biologic agent such as a growth factor, biologic adhesive or binding substance may be added. The bone graft material 500 is contained within the syringe 110 between the plunger head 115 and the end cap 400. The bone graft material 500 is bounded by the plunger head 117 shown positioned near the lumen second end 111b. The plunger head 117 has a periphery which seals against the interior wall 111f of the lumen body 111. The end cap 400 is provided to cover the opening 113 at the first end or delivery end 111a, and is removable prior to use of the loaded syringe 110. The end cap 400 preferably is constructed from a silicone or rubber material that is inert or does not react with the bone graft material 500 or any of the treatment agents (e.g., growth factor) that are added to or required to be added to the bone graft material 500. The cap 400 may be secured to the lumen end 111a using any suitable means, such as for example, tension, pressure or friction, adhesive, heat, a band, retainer or the like, or combinations of these. The bone graft material 500 may be stored in the syringe 111, and the syringe 110 may be shipped and delivered to end users, preloaded with bone graft material 500, and with the plunger 115 installed in the syringe lumen cavity 111c and the end cap 400 secured to the open end 111a. The cap 400 may be configured to have a profile that matches the opening 113, such as, for example, where the opening is cylindrical, elliptical, flat, or combinations of these shapes, and the cap 400 also is secured over the opening 113, and fits the leading edge or projection, such as a bevel at the end of the lumen 111. The end cap may be configured to match the profile of the lumen projection, and fit over the projection and seal the lumen opening. Growth factor solutions, for example, may be injected through the end cap 400. According to some embodiments, the end cap 400 is provided with a preferred area that comprises a puncturable area, see e.g., the area 400a in FIG. 5). The cap 400 may therefore contain the bone graft material 500, as well as any liquid injected into the cavity 111c, such as the growth factor, within the lumen 111. The contents of the syringe 110 are sealed, and provide for the bone graft material to be deposited in the lumen 111 and stored and shipped for distribution to end users.

The syringes according to the invention, such as those syringes 110, 210, 310, 410, 510 and 610 shown in the exemplary embodiments, also may be packaged is a sealed packaging or container, or otherwise encased, such as, in airtight or vacuum type packaging, to further protect the syringe and its contents. The sealed syringe (sealed by the plunger head, and with an end cap) may be packaged in packaging that may be removable from the syringe, or from which the syringe may be removed when it is needed for use.

Figure 6:
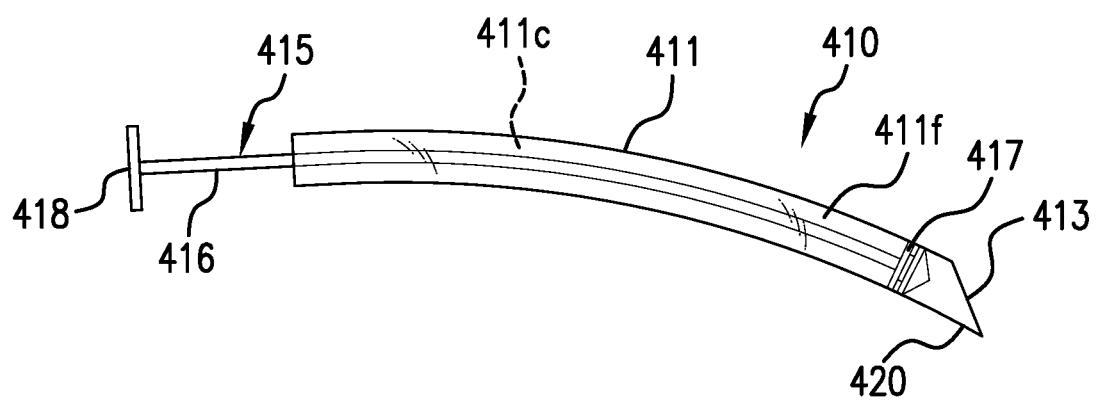
FIG. 6 is a perspective view of a fourth alternate embodiment of a subperiosteal syringe according to the invention.

As shown in FIG. 6, a fourth alternate embodiment of a subperiosteal syringe 410 according to the invention is shown. The syringe 410 is similar to the other embodiments, and may have one or more of the shapes, including elliptical, round, flat-sided, or combinations thereof, where the lumen is curved to arc over its length. The curvature or arc may be uniform, such as radially configured, or may be non-uniform, with multi radial curvatures. The plunger 415 preferably is configured to correspond to the lumen inner profile, and make a seal against the lumen interior wall. The plunger 415 preferably is constructed so that the plunger shaft 416 fits within the curved lumen 411, and may move the plunger head 417 through the curved lumen cavity 411c. The plunger shaft may comprise a coil, curved element, or flexible element that is capable of movement within the confines of the curved lumen cavity 411c, and to provide a force, when depressed, to move the plunger head 417 forward in the lumen 411. Preferably, the plunger head 417 may move beyond the opening 413. The actuator 418 is shown provided at the end of the plunger 415, opposite the end of the plunger head 417. The lumen opening 413 may be provided with a leading portion 420. The curved embodiment may be constructed with any of the preferred shapes, such as those shown and described herein in connection with the embodiments of the subperiosteal syringes 110, 210, 310 shown and described herein. For example, according to one embodiment, the curved syringe 410 may include a syringe lumen 411 with a flat side, such as, for example, the side 411f shown in FIG. 6, which may be inserted and guided along the bone side of a subperiosteal tunnel within which the subperiosteal syringe is guided. Alternatively, the lumen may be elliptically configured, or have a circular lumen body. The plunger may be radial, and, where a curved syringe embodiment is constructed with a lumen is not consistently radial along its length, the plunger may be provided to be moved along the lumen cavity (such as the cavity 411c shown in FIG. 6), by providing the plunger shaft as a coil, or comprised of compressible portions or members that provide suitable rigidity for moving the plunger head forward in the lumen and expressing the syringe contents, while being able to move through the lumen cavity 411c. According to embodiments, the lumen 411 may be provided to have an extended portion, such as the extended portion 420 shown in FIG. 6, which is provided on the opposite longitudinal side of the lumen 411 that is designed to be closest to the bone side of a tunnel within which the subperiosteal syringe, such as the syringe 410, is inserted. Although the subperiosteal syringe 410 is shown in FIG. 6 having a curvature, the curvature may be less pronounced than what is illustrated in the exemplary embodiment. In addition, the curvature may be provided to curve in another direction, such as an opposite direction. The curved subperiosteal syringe also may be constructed with the lumen protruding portion (at the lumen opening) provided as a radially inner portion, versus a radial outward portion (e.g., FIG. 6), where the radially outer portion ends before the radially inner portion to form a beveled opening with a different orientation.

Figure 7A:
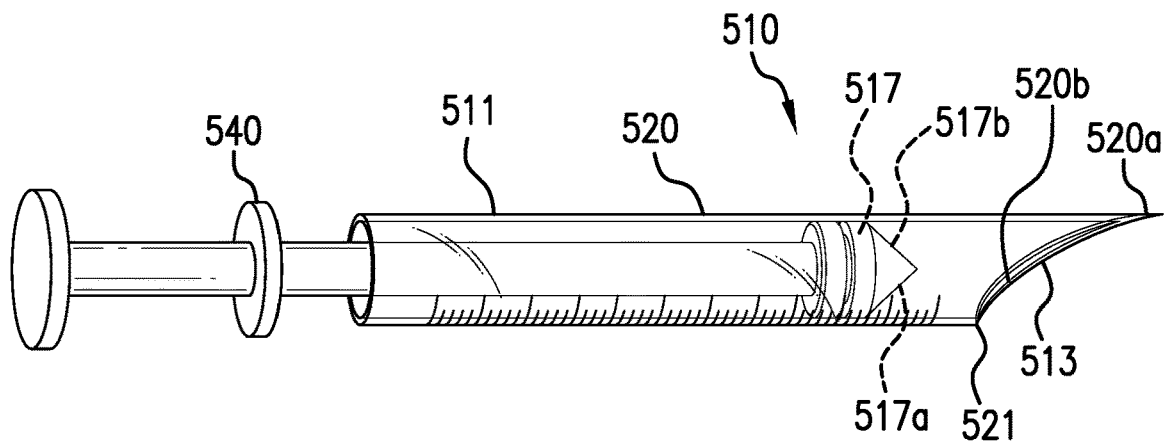
FIG. 7A is a perspective of a fifth embodiment of a subperiosteal syringe device according to the invention, as viewed looking from the right side.
Figure 7B:
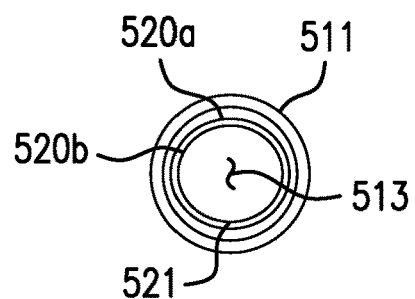
FIG. 7B is an end view of the syringe of FIG. 7A as viewed looking from the end of the syringe.

According to embodiments, the syringe bevel may be curved between the leading end of the lumen body and the trailing end where the opening begins. Turning to FIG. 7A, an alternate embodiment of a syringe 510 is shown. The syringe 510 is illustrated with the leading portion 520 having a leading edge 520a, and a trailing edge 521 where the front opening 513 begins. The leading edge 520a, is arcuate, as shown in the front end view of FIG. 7B. The lateral portion of the lumen that connects the leading edge 520a with the trailing edge 521 is shown having a curved configuration, which, in the example illustrated, has a profiled edge 520b at the opening 513 that curves inwardly or concave with respect to the lumen body 520. The syringe is illustrated in a side elevation view, and may be symmetrical having a respectively similar curved portion on the other side. According to preferred embodiments, the syringe bevel may be angled equal to or greater than about 60 degrees.

According to some alternate embodiments, the syringe may have a first curved portion, such as the curved profiled edge 520b on one side and have a non symmetrical profiled edge on the other side. This embodiment is designed to guide the expression of the syringe contents in a direction away from the leading portion and any extended side portion or profile. For example, a profiled edge on one side may be recessed or curved into the body 520 more than the profiled edge on the other side.

The embodiments of the syringes may include a mechanism, such as, for example, a stop, to prevent the plunger movement from moving beyond a predetermined position or distance. In the embodiment illustrated in FIGS. 7A and 7B, the plunger is shown with the plunger seal or head portion 517 extending to the trailing edge 521 of the syringe 510. In the embodiment illustrated, the plunger head 517 has a tapered portion 517a with a pointed end 517b to break up particles engaged by the plunger head 517. The profile of the plunger head, preferably is conical or has a sloped surface configuration. According to some embodiments, the plunger head profile at the leading end aligns with the bevel profile angle of the lumen 520.

Figure 7C:
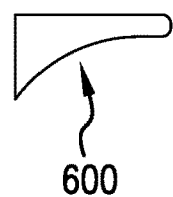
FIG. 7C is a view of an exemplary depiction of an end cap for the syringe of FIG. 7A.

The end cap 600 (FIG. 7C) preferably may be configured having a shape that matches the bevel profile to provide a seal over the lumen end opening 513.

Figure 8A:
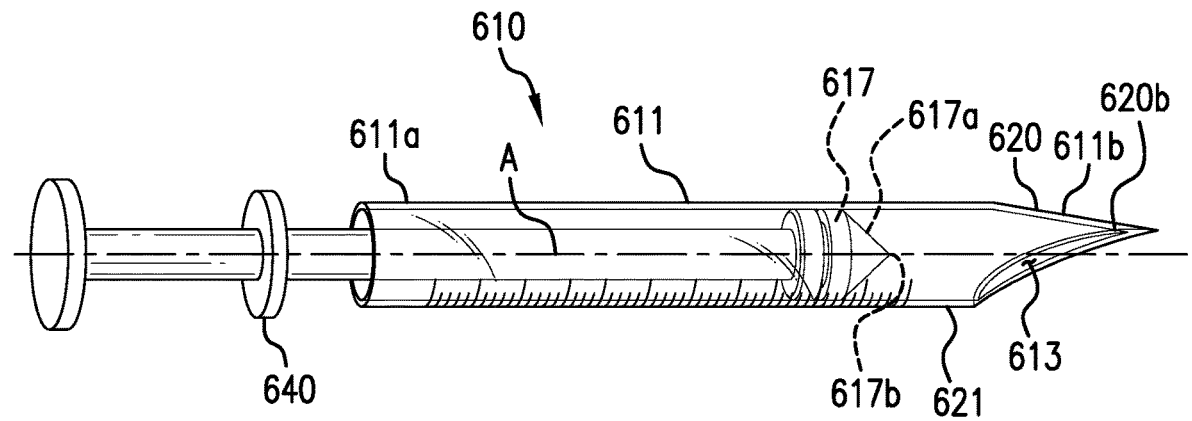
FIG. 8A is a perspective of a sixth embodiment of a subperiosteal syringe device according to the invention, as viewed looking from the right side.
Figure 8B:
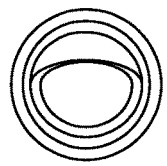
FIG. 8B is an end view of the syringe of FIG. 8A as viewed looking from the end of the syringe.
Figure 8C:
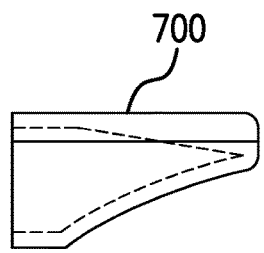
FIG. 8C is a view of an exemplary depiction of an end cap for the syringe of FIG. 8A.

According to another alternate embodiment, a syringe 610 is provides. The syringe 610 includes a leading portion 620 having a bevel at the end of the syringe which forms the opening 613. In the embodiment illustrated, the bevel is shown having a curved profile, with the opening 613 spanning from the end of the leading edge 620 to the trailing edge 621. The upper leading portion 620a is shown being tapered inwardly toward the central axis A of the syringe 610. The inward taper directs the bone material expressed from the syringe 610 in a directional manner, which preferably is toward the bone surface. According to preferred embodiments, the plunger head 617 has a tapered portion 617a and a pointed leading end 617b, and preferably extends to the end of the lumen opening 613. According to some preferred embodiments, the plunger head 617 preferably may be configured to align with the taper of the bevel and particularly with the upper leading portion 620a. For example, according to some embodiments, the plunger taper 617a may engage the interior 620b of the leading portion 620a. According to some embodiments, the plunger head configuration may be profiled to correspond with the taper or profile of the upper leading portion 620a so that the plunger head 617a, or portion therefor, may sealingly engage the interior surface 620b of the lumen of the leading portion 620a. Similarly, an end cap 700 (FIG. 8C) may be configured to fit onto the leading end 620 of the syringe 610.

Syringes preferably may include a stop mechanism to limit the movement of the plunger. For example, in FIG. 7A a stop mechanism is shown comprising a stop element 540 disposed on the plunger shaft 516, which is situated a distance from the plunger end so as to limit the travel of the plunger head, and provide the limit position of the plunger. For example, according to some preferred embodiments, the syringes disclosed herein may be provided with a stop mechanism, and the plunger head may be limited and controlled by the stop mechanism to prevent its travel beyond the lumen opening 513. Similarly, the other syringes shown and described herein also may be provided with a stop mechanism to limit the plunger travel. For example, the stop mechanism may limit the plunger head travel to a location at or before the beginning of the lumen opening. In the embodiment of the syringe 610 shown in FIGS. 8A, 8B and 8C, the plunger travel may be limited by the bevel leading portion 620. The plunger head 617 may engage with the inwardly tapered wall of the leading portion 620 to stop further travel of the plunger 615. Alternatively or in addition, the syringe plunger 615 may be provided with a stop mechanism, such as, for example, the stop 640.

The syringes shown and described herein, although depicted with a straight profile at the opening, may be configured with a curved profile opening, including, for example, the curved profile shown and described in the syringe embodiments 510 and 610 of FIGS. 7A-7C and 8A-8C, respectively. In addition, syringes shown and described herein, although depicted with a parallel leading edge profile at the opening, may be configured with an inwardly tapered or angled leading portion, including, for example, the inwardly tapered angled profile shown and described in the syringe embodiment 610 of FIGS. 8A-8C.

Figure 9:
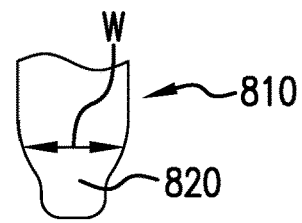
FIG. 9 is a partial view of an alternate embodiment of a syringe showing an alternate end configuration as viewed from the top, the syringe end being shown separate from the plunger and remainder of the lumen body.

Embodiments of the syringes may provide variations of the bevel, with some bevels having a bevel profile, when viewed from the side, that is straight, while other embodiments provide a bevel profile that is curved. Alternate embodiments may be configured the leading edge of the bevel to have more area so that bone material expressed from the syringe lumen opening 613 may be directed by the leading portion. For example, the leading edge may include a leading portion that is partially cylindrical, or radial in cross section (taken perpendicular to the syringe central axis A). FIG. 9 illustrates an alternate configuration for the leading portion which may be tapered or angled, or straight, which has a widened leading portion 820 as shown by the double arrow W.

The syringes may be constructed with one or more combinations of the features disclosed herein. For example, some embodiments may provide a syringe having a straight leading edge with straight bevel. For example, the bevel may have a profile that provides a linear dimension when viewing the syringe from the side from the leading edge to a trailing edge at the syringe opening. Alternatively, the syringe may be constructed having a straight leading edge with a concave bevel, so that the side profile of the syringe exhibits a concavity from the leading edge to the trailing edge at the syringe opening. According to other embodiments, the syringe may be constructed with an angled leading edge, which preferably is angled toward the central axis of the syringe lumen. The angled leading edge may be provided with a bevel profile, as viewed from a side view that is straight from the angled leading edge to the trailing edge, or according to an alternate configuration where the bevel profile is concave from the leading edge to the trailing edge. The degree of concavity may be provided and may be a uniform arc or radius, or, according to some embodiments may have multiple radial portions over its dimension. For example, the profile may provide a larger radial degree at a portion closer to the leading edge of the bevel, and may provide a smaller radial dimension at the portion closer to the trailing edge. Other embodiments may be skewed inwardly, so the radial bevel profile is pulled inwardly of the opening, relative to a straight line profile from the leading edge to the trailing edge. In the syringes shown and described herein, the leading edge is designed to provide a smaller profile for the leading portion of the syringe to enter the tunnel via the remote incision while also providing the ability to elevate the mucosa and the periosteum when the syringe is inserted into a remote incision and maneuvered through the subperiosteal tunnel. According to some embodiments, the inward taper of an angularly provided beveled leading edge may further direct the expressed bone material, such as bone particles, to the bone surface.

As with the syringes disclosed herein, the bevel configuration facilitates insertion into the laparoscopic tunnel, and providing the leading portion serves to elevate the mucosa. The leading edge is configured to direct the bone particles to the bone surface.

Alternative embodiments include the use of surgical navigation or laparoscopic camera systems to assist in maneuvering the syringe within the subperiosteal tunnel, and delivering the bone graft particles within the subperiosteal pouch. The surgical navigation and laparoscopic equipment may be attached to the subperiosteal syringe, or incorporated into the design of the subperiosteal syringe. For example, a portion of the syringe body that remains external to the subperiosteal tunnel may be modified to accept the attachment of positioning devices as part of a surgical navigation system. An alternative embodiment may include an endoscopic or laparoscopic camera assembly that is attached or incorporated into the body of the subperiosteal syringe.

According to some preferred embodiments, as shown in the exemplary embodiments illustrated, the subperiosteal syringes 110, 210, 310, 410, 510 may be constructed having a cross-sectional profile that has a uniform width along the length of the lumen 111, 211, 311, 411, 511. According to preferred embodiments, the lumen cross-sectional profile preferably is maintained along the length of the lumen body through the delivery end of the lumen, and at the delivery end opening. A leading portion of the lumen that forms the projection, according to preferred embodiments, may be dimensioned within the lumen cross-sectional profile, to represent the cross-sectional profile over its extended length. According to alternate embodiments, such as the syringe 610 (FIGS. 8A-8C), the cross-sectional profile may be uniform with the leading portion having a different cross-sectional profile.

According to some embodiments, a syringe, such as, for example, any of those syringes 110, 210, 310, 410, 510, 610 is provided with a lumen (111, 211, 311, 411, 511, 611) having bone graft material 500 therein. The bone graft material may comprise particulate bone matter, or, according to some alternate embodiments, may comprise a bone substitute in paste form. The bone graft material may include bone particles that are provided in a size range between about 0.25 and 1.0 mm in diameter, and preferably may be provided within a range of about 0.50 to 1.0 mm in diameter (the diameter being a rough diameter for bone particle measurement as the particles are not typically uniform). An amount of about 0.25 grams to about 0.5 grams of the bone particles are pre-loaded into the subperiosteal syringe (such as those 110, 210, 310, 410, 510, 610), although alternative embodiments may include larger amounts of bone particles. The bone particle granules (particulate bone material) remain loosely packed in the syringe. An end cap, such as the cap 400, is provided to seal the subperiosteal syringe opening against intrusive materials (e.g., air and moisture) as well as to prevent leakage of the bone graft material out from the syringe. According to some embodiments, the bone material may be supplied in the syringe along with another substance, such as, for example, a growth factor, collagen, a biologic adhesive or binding agent. The pre-loaded syringe may be provided with desired bone material, such as, for example, bone particle graft material (e.g., based on size or amount) or bone paste, and may be delivered to the medical personnel user or facility and stored until needed. A liquid substance may be administered to the bone graft material in the syringe by admitting it through the plunger head, and more preferably, by injecting it using a needle that is inserted through the plunger head. In addition, the end cap 400 may be removed to permit a suitable instrument to be inserted (if needed or desired), to mix or break up any agglomerations of particles that may have formed during storage or shipping. The syringe embodiments shown and described herein may be used to conduct jaw, face, or bone reconstruction procedures, where augmentation of the bone is accomplished by introducing bone graft material to the surgical site. According to some preferred implementations, the syringes are useful for maneuvering the lumen containing bone graft material through a tunnel developed at the surgical site that leads to a pocket or pouch where the bone material is desired to be deposited in order to develop the bone at that location (which may augment the existing bone of the patient). This procedure may be carried out to install implants, and synthetic teeth in the mouth of a patient, to augment facial bones to support facial tissues and enhance facial esthetics, or to augment bone in any location within the body where a subperiosteal approach is advantageous. The bone graft material, according to some embodiments, may comprise a paste which may comprise a binding or adhesive agent mixed with bone particles, and which, according to some embodiments, may further include one or more of collagen and/or growth factors. The syringe may be provided with the bone paste, and/or one or more of the optional materials. Alternatively, bone paste material may be activated with a catalyst so that the bone paste will set in a solid or semi-solid form following its application to the surgical site. The catalyst, for example, according to some embodiments, may be provided to trigger a biologically beneficial chemical reaction, such as, for example, the release of a substance, such as growth factors. According to some embodiments, the catalyst may be injected into the syringe lumen (where the bone material is contained) through the sealing cap (such as, for example, the cap 400) at the end of the syringe.

According to some alternative embodiments, the syringe may be constructed with a mixing mechanism incorporated into the syringe, so that both bone material and a catalyst or other substance desired to be kept separate from each other until use, may be separately stored in separate compartments within the syringe, and may be brought together in the syringe when desired (when ready to be used). For example, according to an alternate embodiment, the mixing mechanism may comprise an automatic mixing mechanism that is incorporated into the syringe, whereby pressure from the plunger causes a base (of bone material or paste) and catalyst to flow from separate chambers into an automixing spiral mechanism. Preferably the separating and mixing mechanisms, including the automixing mechanism, are contained within the syringe. According to this alternate embodiment, the syringes may be configured to contain separate component chambers loaded with separate components (bone material/paste in one chamber, and growth factor and/or catalyst in another).

According to preferred embodiments, the subperiosteal syringe is configured to promote a uniform expression of the bone graft material from the lumen body to the surgical site. As depicted in the subperiosteal syringe exemplary embodiments 110, 210, 310, and 410 shown and described herein, the lumen body preferably provides an unobstructed pathway for the bone material to move through. The subperiosteal syringes are configured to express the bone material from the syringe into the surgical site by controlling the depression of the plunger. The protruding end portion and lumen passageway control the expression of the bone material from the lumen by directing the material toward the bone. Referring to FIG. 5, bone material, such as bone particulate material, preferably is loaded into the syringe lumen body. According to some preferred embodiments, the lumen body is dimensioned to accommodate bone particles ranging between about 0.25 and 1.0 mm in diameter. Some preferred dimensions for the subperiosteal syringes include lumens having diameters from between about 2 to 7 mm, and preferably from about 3 to 6 mm, and more preferably from about 3.5 to 5.5 mm. According to some embodiments, the syringe diameter may be between about 3 to 4 mm. According to some embodiments, where the lumen is provided having an elliptical configuration, the width of the elliptical lumen body preferably is greater than the height. The width preferably spans the longitudinal direction and includes the protruding portion (see e.g., the leading portion 220 in FIGS. 3A, 3B and 3C). The width is represented by a double arrow 251 (FIG. 3C) and the height is represented by the double arrow 250 (FIG. 3B). According to a preferred embodiment, the width to height ratio is from about 2:1 to about 4:1, with a preferred range being about 3:2. According to a preferred embodiment, a subperiosteal syringe is configured having a height of about 3.5 mm and a width of about 5.5 mm. Preferably the height and width dimensions may be internal dimensions. For example, the elliptically configured subperiosteal syringe 210 shown in FIGS. 3A-3D, may be constructed with a height 250 (FIG. 3B) of about 3.5 mm and a width 251 (FIG. 3C) of about 5.5 mm. For example, according to one proposed example, bone graft material in the form of particulate bone in an amount of from between about 0.25 grams to about 0.5 grams, and having diameter ranges from between about 0.25 to 1.0 mm, is loaded into the lumen of a subperiosteal syringe having an elliptical configuration, such as the subperiosteal syringe 210 shown and described herein, with a height of about 3.5 mm and a width of about 5.5 mm, and an overall length of about 15 cm, with the plunger positioned 3 cm of the 15 cm length, providing 12 cm of lumen length in which the bone material is loaded.

The volume occupied by the bone material, in this proposed example, is V, which may be determined by expression (1):

$$V = \pi WHL/4 \quad (1),$$

where V is the volume, W is the width of the elliptical lumen, H is the height of the elliptical lumen, and L is the length of the lumen (that the bone material will occupy). Applying the formula to the proposed subperiosteal syringe, $$V = \pi * 5.5 * 3.5 * 12/4$$

$$V = 181.5 \text{ cubic mm (or mm}^3\text{)}.$$

It is noted that the lumen end portion that is beveled may be subtracted from the final value V to make an adjustment due to the sloped end. Alternatively, the lumen length is taken at a point midway of the protrusion of the leading projection.

Taking the volume of 181.5 mm^3, and the bone graft material being between about 0.25 g to 0.5 g, the bone material density within the lumen may be determined. Taking 0.25 g/181.5 mm^3 results in 0.00138 g/mm^3, and taking 0.5 g/181.5 mm^3, results in twice the value or 0.00275 g/mm^3. According to the proposed example, bone particle material is loaded in the syringe at a density of from about 0.00138 g/mm^3 to about 0.00275 g/mm^3.

Alternatively, the bone graft material may be provided in the form of particulate bone material, in a density of from about 0.001 to about 0.005 g/mm^3.

According to preferred embodiments, the subperiosteal syringes, such as those 110, 210, 310, 410, 510 and 610, shown and described herein, may be constructed with lengths suitable to reach the surgical site where the syringe contents, namely, the bone material, will be deposited. The subperiosteal syringes 110, 210, 310, 410, 510, 610 are configured to be maneuvered through a subperiosteal tunnel. According to some preferred embodiments, syringes may be constructed with lumen lengths of from about 5 to 20 cm, and preferably from about 5 to 15 cm, with the lengths being measured from the tip of the end of the lumen barrel to the tip of the syringe. The subperiosteal syringe diameters, which preferably may be internal diameters, preferably range from about 3 to 8 mm, and more preferably from about 3 to 6 mm. The syringe diameters according to preferred embodiments are provided along the length of the lumen.

The syringes shown and described herein preferably are constructed from a material that allows visibility into the lumen cavity. The material from which the subperiosteal syringe lumen is constructed minimizes or eliminates fractures and/or shearing when the syringe is in use, and prevents or minimizes separation of the assembly parts. The syringe lumen (such as, the lumen 111, 211, 311, 411, 511, 611) preferably is constructed from a suitable material that provides maneuverability of the syringe through the subperiosteal tunnel. According to preferred embodiments, the plunger may be provided as a monolithic plunger, which includes a plunger head, shaft and actuation end that preferably are provided a single component. Alternatively, some embodiments of the plunger may be comprises as a single component, where the molding material may be different for parts of the plunger (e.g., actuator, shaft, and/or head). For example, the syringe lumen body preferably may be constructed from any suitable material that is sufficiently rigid to be maneuvered through a subperiosteal tunnel, while at the same time permitting some flexibility. The plunger is provided to glide smoothly within the lumen, with light to moderate pressure, allowing for the controlled expression of the graft material into the subperiosteal pouch or tunnel.

According to preferred embodiments, the plunger shaft is sufficiently flexible to allow bending under a certain degree of pressure that may be encountered when the graft material has been packed with excessive density, therefore preventing a burst of the graft material from being suddenly expressed into the subperiosteal pouch or tunnel. Some examples of suitable materials are plastic materials, which may be used to construct the lumen body. The plunger may be formed from a rubber, silicone, or other suitable material that is capable of providing a seal against the lumen body interior. The materials used for the plunger and lumen are selected to be inert or non-reactive to the bone graft material and any agent added thereto, as well as to sterilization substances or procedures used to prepare and/or load the syringe. The subperiosteal syringe lumen may be produced by extrusion, injection molding, or other suitable process. The plungers shown and described herein may be produced using similar methods, any, optionally, may be produced using overmolding to provide more rigidity to one or more portions of the plunger, such as, the actuator, shaft, head, or portions and/or combinations thereof. The subperiosteal syringes preferably are provided for a single use, and are discarded after use.

The subperiosteal syringe device contents, such as particulate bone material, are expressed from the opening in the lumen through the actuation of a plunger. The plunger is depressed to deliver bone graft material from the syringe to the location where the syringe lumen opening is positioned (e.g., within the patient). The plunger head may be configured to control the rate or dispersion of the material from the syringe. Examples of plunger heads are depicted according to preferred embodiments as being tapered, with a tapered end centrally positioned, relative to the lumen opening. The markings on the syringe lumen body may be used to provide a measurement of the penetration depth of the syringe into a tunnel, or a volume of material loaded into or dispersed from the syringe. The syringe may be withdrawn a known distance, for example 1.0 cm, based on the markings provided on the lumen body, so that during the withdrawal of the syringe, the contents may be expressed to deliver content along the 1.0 cm withdrawal path. The syringe volumetric markings may provide an indication of the amount of material expressed from the syringe, e.g., into the surgical site.

Features discussed and shown herein in conjunction with one or more embodiments of the syringe devices may be combined with one or more features and implemented together. In addition, although not shown, accessories, including mechanisms may be configured to provide actuation of the plunger to express material from the syringe. This may be accomplished through the coupling of an electronic control to drive the movement of the plunger. The control may be provided as a button or switch that the user may affix to an instrument, or comprise a foot switch or other means of actuations. The lumens are shown having a protruding portion, and although shown and described in an exemplary embodiment having an angle at about 45 degrees, however, other bevel angles are possible. For example, the lumen may be provided having a smaller angle (relative to the protruding lumen profile) so that the protruding portion of the lumen extends further from the trailing portion, to increase the bevel, thereby reducing the angle that the tip makes with the trailing lumen. For example, according to some alternate embodiments the bevel angle may be between about 30 to 35 degrees. According to preferred embodiments disclosed, the amount of bone material provided in the subperiosteal syringe, preferably is between about 0.25 and 0.5 g of bone material (such as bone particles), however, according to some alternative embodiments, bone material (such as bone particles) may be provided in the syringe lumen at amounts of up to 1.0 g. In addition, although described in connection with delivering bone material to augment the existing bone by developing a tunnel and pouch at a location to deliver bone graft material between the bone and the periosteum, alternatively, the syringes may be used to deliver bone material to an already existing implant that is lacking in bone e.g., as a result of improper placement, or bone loss that has taken place over the years. While the devices of the invention have been disclosed in detail, and the preferred embodiments and best mode for practice of the invention have been similarly disclosed, the scope of exclusive rights to which the invention is entitled is defined by the claims appended hereto and by equivalents that perform substantially the same function in substantially the same way to achieve the same result.

What is claimed is:

1. A subperiosteal syringe-elevator assembly for separating the periosteum and admitting particulate bone graft material within a subperiosteal tunnel, comprising:
    a) a lumen body having an insertable portion;
    b) the lumen body having a first opening that is configured for insertion into the subperiosteal tunnel and for expressing particulate bone graft material to exit the syringe-elevator through said first opening, and a second opening configured to remain outside the subperiosteal tunnel during use;
    c) the lumen body having a cavity therein with an uninterrupted surface and a continuous diameter;
    d) a plunger sealingly engaging the lumen cavity and being sized to fit within the lumen cavity, and that is introduced through the second opening;
    e) the lumen terminating at the first opening and having a leading elevator portion that at the first opening extends longitudinally beyond another lumen portion and is used to gain access to the subperiosteal tunnel;
    f) wherein the lumen body is a sufficiently rigid monolithic structure having a continuous lumen wall without a stepped portion, said wall forming said leading portion, and wherein said leading portion comprises a leading edge;
    g) wherein said lumen wall has a cross-sectional profile having a uniform width along the insertable portion of the lumen body; and
    h) wherein said lumen first opening is beveled at the point of exit.

2. The subperiosteal syringe-elevator assembly of claim 1, wherein said plunger has an actuator.

3. The subperiosteal syringe-elevator assembly of claim 2, wherein the plunger is movable within the lumen cavity to slide a predetermined distance through the lumen cavity.

4. The subperiosteal syringe-elevator assembly of claim 3, wherein said first opening is configured for delivery of material from said lumen cavity, wherein said first opening is defined by said lumen wall, wherein said plunger has a plunger head, and wherein said plunger is movable to extend the plunger head to a position that is at least partially beyond the lumen wall forming the first opening.

5. The subperiosteal syringe-elevator assembly of claim 1, wherein said lumen includes a first portion and a second portion, wherein at the first opening said lumen first portion includes a projecting portion that projects beyond the lumen second portion.

6. The subperiosteal syringe-elevator assembly of claim 5, wherein said lumen wall has a longitudinal length, and wherein said plunger path of travel is coextensive with said lumen wall longitudinal length.

7. The subperiosteal syringe-elevator assembly of claim 1, wherein said lumen has a non-cylindrical cross-sectional profile.

8. The subperiosteal syringe-elevator assembly of claim 7, wherein said lumen has an elliptical profile.

9. The subperiosteal syringe-elevator assembly of claim 1, wherein the first opening comprises an opening for expressing the subperiosteal syringe-elevator contents therethrough, the subperiosteal syringe-elevator including plurality of markings that indicate a distance from a respective one of the markings to the subperiosteal syringe-elevator end having the first opening, wherein said markings provide an indication of the subperiosteal syringe-elevator insertion depth.

10. The subperiosteal syringe-elevator assembly of claim 1, including an end cap, and bone graft material disposed within the lumen and bounded between the plunger at one end of the lumen and the end cap at the other end of the lumen.

11. The subperiosteal syringe-elevator assembly of claim 10, wherein the bone graft material comprises particulate bone particles.

12. The subperiosteal syringe-elevator assembly of claim 10, wherein the bone graft material comprises a bone substitute or synthetic bone paste.

13. The subperiosteal syringe-elevator assembly of claim 10, including one or more substances selected from the group consisting of growth factors and collagens.

14. The subperiosteal syringe-elevator assembly of claim 10, wherein the bone graft material disposed within the lumen and bounded between the plunger at one end of the lumen and the end cap at the other end of the lumen is provided in an amount of 0.25 g to 1.0 g, and wherein the bone graft material comprises one or more of particulate bone particles, a bone substitute, or a synthetic bone paste.

15. The subperiosteal syringe-elevator assembly of claim 14, wherein the bone graft material is bone particles having an average particle size diameter range from between about 0.25 and 1.0 mm.

16. The subperiosteal syringe-elevator assembly of claim 1, wherein said lumen has a width and a height, and wherein said leading portion is provided between the width and defines a top of the height.

17. The subperiosteal syringe-elevator assembly of claim 16, wherein said ratio of the width to the height is from about 2:1 to about 4:1.

18. The subperiosteal syringe-elevator assembly of claim 16, wherein said width is about 5.5 mm and wherein said height is about 3.5 mm.

19. The subperiosteal syringe-elevator assembly of claim 16, wherein said lumen cavity has an interior surface, wherein said lumen wall has a longitudinal length, wherein the lumen height is coextensive along the lumen longitudinal length, wherein the lumen width is coextensive along the lumen longitudinal length, and wherein said plunger path of travel is coextensive with said lumen wall longitudinal length, wherein the plunger path of travel is defined by the lumen height and lumen width, wherein the plunger has a head making a seal against said lumen cavity interior surface, and wherein said plunger head has a width and height ratio that is coextensive with the cross-sectional ratio of the lumen width and height.

20. The subperiosteal syringe-elevator assembly of claim 16, wherein said density of bone particle material in said syringe-elevator lumen is from about 0.001 to about 0.005 g/mm3.

21. The subperiosteal syringe-elevator assembly of claim 1, wherein the lumen has a longitudinal length and is curved to arc along its longitudinal length, and wherein the plunger is configured to move through the curved lumen.

22. The subperiosteal syringe-elevator assembly of claim 1, wherein said first opening has a curved profile.

23. The subperiosteal syringe-elevator assembly of claim 1, wherein said lumen body comprises a longitudinal length with at least one first portion of said longitudinal length spanning in a longitudinal direction, and at least one second portion of said longitudinal length spanning in a longitudinal direction parallel to the first portion; wherein said second portion of said longitudinal length extends longitudinally beyond said first portion of said longitudinal length to form the first opening, wherein said second portion of said longitudinal length forms the leading portion and extends longitudinally beyond said first portion of said longitudinal length.

24. The subperiosteal syringe-elevator assembly of claim 23, wherein said second portion of said longitudinal length that extends longitudinally beyond said first portion of said longitudinal length to form the first opening is inwardly tapered.

25. The subperiosteal syringe-elevator assembly of claim 23, wherein said lumen has an elliptical profile.

26. The subperiosteal syringe-elevator assembly of claim 25, wherein said second portion of said longitudinal length that extends longitudinally beyond said first portion of said longitudinal length to form the first opening is inwardly tapered.

27. The subperiosteal syringe-elevator assembly of claim 1, wherein said lumen opening opens in the direction of said longitudinal length.

28. The subperiosteal syringe-elevator assembly of claim 1, wherein the plunger travel includes travel within the insertable portion of the lumen body.

29. The subperiosteal syringe-elevator assembly of claim 1, wherein the second opening, and wherein the syringe-elevator is sealed with the plunger head and an end cap.

30. The subperiosteal syringe-elevator assembly of claim 1, wherein the lumen body continuous wall has a continuous diameter.

31. A subperiosteal syringe-elevator assembly for separating the periosteum and admitting particulate bone graft material within a subperiosteal tunnel, comprising:
   a) a lumen body having an insertable portion;
   b) the lumen body having a first opening that is configured for insertion into the subperiosteal tunnel and a second opening configured to remain outside the subperiosteal tunnel during use;
   c) the lumen body having a cavity therein with an uninterrupted surface and a continuous diameter;
   d) a plunger sealingly engaging the lumen cavity and being sized to fit within the lumen cavity, and that is introduced through the second opening;
   e) the lumen terminating at the first opening and having a leading elevator portion that at the first opening extends longitudinally beyond another lumen portion and is used to gain access to the subperiosteal tunnel;
   f) wherein the lumen body is a sufficiently rigid monolithic structure having a continuous wall without a stepped portion, said wall forming said leading portion, and wherein said leading portion comprises a leading edge; and g) wherein said lumen wall has a cross-sectional profile having a uniform width along the insertable portion of the lumen body;

h) wherein said lumen cavity has a first end and a second end, wherein said lumen cavity is sealed at each end thereof; and wherein said device includes a mechanism for admitting a liquid into said sealed lumen cavity.

32. The subperiosteal syringe-elevator assembly of claim 31, wherein said plunger seals at least one end of said lumen cavity and wherein an end cap seals at least the other end of said lumen cavity.

33. The subperiosteal syringe-elevator assembly of claim 32, wherein said mechanism for admitting a liquid into said lumen cavity is provided in said end cap.

34. A subperiosteal syringe-elevator assembly for separating the periosteum and admitting particulate bone graft material within a subperiosteal tunnel, comprising:
a) a lumen body having an insertable portion;
b) the lumen body having a first opening that is configured for insertion into the subperiosteal tunnel and a second opening configured to remain outside the subperiosteal tunnel during use;
c) the lumen body having a cavity therein with an uninterrupted surface and a continuous diameter;
d) a plunger sealingly engaging the lumen cavity and being sized to fit within the lumen cavity, and that is introduced through the second opening;
e) the lumen terminating at the first opening and having a leading elevator portion that at the first opening extends longitudinally beyond another lumen portion and is used to gain access to the subperiosteal tunnel;
f) wherein the lumen body is a sufficiently rigid monolithic structure having a continuous wall without a stepped portion, said wall forming said leading portion, and wherein said leading portion comprises a leading edge; and
g) wherein said lumen wall has a cross-sectional profile having a uniform width along the insertable portion of the lumen body; and
h) wherein said lumen comprises a longitudinal length with at least one first portion of said longitudinal length spanning in a longitudinal direction, and at least one second portion of said longitudinal length spanning in a longitudinal direction parallel to the first portion, wherein said first portion comprises a flat portion, and wherein said second portion comprises a curved portion.

35. The subperiosteal syringe-elevator assembly of claim 34, wherein said first portion of said longitudinal length and said second portion of said longitudinal length are disposed on opposite sides of the lumen.

36. The subperiosteal syringe-elevator assembly of claim 35, wherein said second portion of said longitudinal length extends longitudinally beyond said first portion of said longitudinal length to form the first lumen opening, wherein said second portion of said longitudinal length forms the leading portion and extends longitudinally beyond said first portion of said longitudinal length.

37. The subperiosteal syringe-elevator assembly of claim 36, wherein the first lumen opening comprises a beveled opening.

38. The subperiosteal syringe-elevator assembly of claim 36, further comprising particulate bone graft material sealingly contained within said lumen.

39. The subperiosteal syringe-elevator assembly of claim 38, further comprising a growth factor within said lumen.

40. The subperiosteal syringe-elevator assembly of claim 39, wherein said lumen is constructed from a material that allows visibility into said lumen cavity.

41. The subperiosteal syringe-elevator assembly of claim 36, further comprising a substitute bone material comprising a paste sealingly contained within said lumen.

42. The subperiosteal syringe-elevator assembly of claim 41, further comprising one or more of a growth factor, collagen, or binding or adhesive agents contained within said lumen along with the bone material.

43. A subperiosteal syringe-elevator assembly for separating the periosteum and admitting particulate bone graft material within a subperiosteal tunnel, comprising:
a) a lumen body having an insertable portion;
b) the lumen body having a first opening that is configured for insertion into the subperiosteal tunnel and a second opening configured to remain outside the subperiosteal tunnel during use;
c) the lumen body having a cavity therein with an uninterrupted surface and a continuous diameter;
d) a plunger sealingly engaging the lumen cavity and being sized to fit within the lumen cavity, and that is introduced through the second opening;
e) the lumen terminating at the first opening and having a leading elevator portion that at the first opening extends longitudinally beyond another lumen portion and is used to gain access to the subperiosteal tunnel;
f) wherein the lumen body is a sufficiently rigid monolithic structure having a continuous wall without a stepped portion, said wall forming said leading portion, and wherein said leading portion comprises a leading edge; and
g) wherein said lumen wall has a cross-sectional profile having a uniform width along the insertable portion of the lumen body;
h) wherein said leading portion of said lumen which at the first opening extends longitudinally beyond another lumen portion, is coextensive with the lumen cross-sectional profile, so as to continue to represent the cross-sectional profile over its leading portion.

* * * * *